(12) United States Patent
Kumagawa

(10) Patent No.: US 10,383,770 B2
(45) Date of Patent: Aug. 20, 2019

(54) AUDITORY SENSITIVITY ADJUSTMENT DEVICE

(71) Applicant: Yosuke Kumagawa, Kanagawa (JP)

(72) Inventor: Yosuke Kumagawa, Kanagawa (JP)

( * ) Notice: Subject to any disclaimer, the term of this patent is extended or adjusted under 35 U.S.C. 154(b) by 6 days.

(21) Appl. No.: 15/594,947

(22) Filed: May 15, 2017

(65) Prior Publication Data

US 2017/0246037 A1 Aug. 31, 2017

Related U.S. Application Data

(63) Continuation of application No. 15/029,890, filed as application No. PCT/JP2014/077657 on Oct. 17, 2014, now Pat. No. 9,717,632.

(30) Foreign Application Priority Data

Oct. 17, 2013 (JP) ................................ 2013-216040

(51) Int. Cl.
*H04R 25/00* (2006.01)
*A61F 11/00* (2006.01)
*G10K 11/26* (2006.01)
*G10K 11/18* (2006.01)

(52) U.S. Cl.
CPC ............ *A61F 11/008* (2013.01); *G10K 11/26* (2013.01); *A61F 11/00* (2013.01); *G10K 11/18* (2013.01)

(58) Field of Classification Search
CPC ........... A61B 1/227; A61B 1/32; A61F 11/08; H04R 25/02
See application file for complete search history.

(56) References Cited

U.S. PATENT DOCUMENTS

| | | | |
|---|---|---|---|
| 3,030,688 A | 11/1860 | Page | |
| 845,383 A | * 2/1907 | Turner et al. | ........... A61F 11/00 601/77 |
| 1,708,257 A | 4/1929 | Campbell | |
| 1,820,107 A | 8/1931 | Agee | |
| 2,537,201 A | 1/1951 | Amfitheatrof | |
| 3,618,698 A | 11/1971 | McCabe | |
| 3,658,150 A | 4/1972 | Turner | |

(Continued)

FOREIGN PATENT DOCUMENTS

DE 322912 7/1920
DE 476991 A 5/1929

(Continued)

OTHER PUBLICATIONS

Japanese Office Action dated Sep. 1, 2015 for the corresponding Japanese Patent Application No. 2013-216040.

(Continued)

*Primary Examiner* — Curtis A Kuntz
*Assistant Examiner* — Ryan Robinson
(74) *Attorney, Agent, or Firm* — Rankin, Hill & Clark LLP

(57) ABSTRACT

Provided is an auditory sensitivity adjustment device suitable to enhance concentration and attentiveness in any direction. An auditory sensitivity adjustment device 100 includes grab parts 32a and 32b for holding a pinna 50, springs 22 for applying to the grab parts 32a and 32b a force for pulling, in an extending direction, the pinna 50 held by the grab parts 32a and 32b, and a base 38 for rotating the pinna 50 held by the grab parts 32a and 32b so as to twist the pinna 50.

4 Claims, 3 Drawing Sheets

(56) References Cited

U.S. PATENT DOCUMENTS

| | | | |
|---|---|---|---|
| 3,938,616 A | 2/1976 | Brownfield | |
| 4,574,912 A | 3/1986 | Fuss et al. | |
| 4,997,056 A | 3/1991 | Riley | |
| 5,020,629 A | 6/1991 | Edmundson et al. | |
| D341,885 S | 11/1993 | Hara | |
| 5,851,177 A * | 12/1998 | Koch | A61B 1/32 600/206 |
| 5,965,850 A | 10/1999 | Fraser | |
| 6,229,901 B1 | 5/2001 | Mickelson et al. | |
| 8,122,995 B1 | 2/2012 | Riley | |
| 9,578,406 B2 * | 2/2017 | Ikeda | H04R 1/1016 |
| 9,717,632 B2 * | 8/2017 | Kumagawa | A61F 11/008 |
| 2002/0062110 A1 | 5/2002 | Sorribes | |
| 2008/0123884 A1 | 5/2008 | Donenfeld et al. | |
| 2010/0059078 A1 | 3/2010 | Winters | |
| 2012/0111659 A1 | 5/2012 | Vogel | |
| 2012/0186898 A1 | 7/2012 | Arietta | |
| 2012/0186899 A1 | 7/2012 | Arrieta | |
| 2012/0186900 A1 | 7/2012 | Arrieta | |
| 2012/0186901 A1 | 7/2012 | Arrieta | |
| 2012/0205189 A1 | 8/2012 | Arrieta | |
| 2013/0098705 A1 | 4/2013 | Arrieta | |
| 2014/0224568 A1 | 8/2014 | Arrieta | |
| 2014/0316456 A1 * | 10/2014 | Ando | A61H 7/004 606/204 |

FOREIGN PATENT DOCUMENTS

| | | |
|---|---|---|
| JP | 646700 | 1/1989 |
| JP | 2003505151 T2 | 2/2003 |
| JP | 2003189398 A2 | 7/2003 |
| JP | 2005266729 A2 | 9/2005 |
| JP | 2012083374 A2 | 4/2012 |
| JP | 2014223280 A2 | 12/2014 |
| WO | 2012100121 A2 | 7/2012 |

OTHER PUBLICATIONS

International Search Report dated Jan. 27, 2015 filed in PCT/JP2014/077657.

Extended European Search Report dated May 29, 2017 for European Patent Application No. 14853206.2.

* cited by examiner

AUDITORY SENSITIVITY ADJUSTMENT DEVICE

TECHNICAL FIELD

The present invention relates to a device for adjusting auditory sensitivity of a human or an animal, more particularly to an auditory sensitivity adjustment device suitable to enhance concentration and attentiveness in any direction.

BACKGROUND ART

A human perceives sound as a result of collection of external sound by the pinna and transmission of the sound to the tympanic membrane through the external auditory canal. In a human, auditory sense gives an effect on his/her concentration and attentiveness. It is known that increasing auditory sensitivity, for example, by enhancing a sound collection effect leads to enhancement of concentration and attentiveness (Patent Literature 1). Also, there is known a headphone-type sound collector capable of effectively collecting a voice coming from the front (Patent Literature 2).

CITATION LIST

Patent Literature

Patent Literature 1: JP-A-2005-266729
Patent Literature 2: JP-A-2012-83374

SUMMARY OF THE INVENTION

Problems to be Solved

However, in the technique disclosed by Patent Literature 1, sound coming from the front and voice uttered by a user are reverberated by side shield plates and are then collected to the user's ear (see paragraph [0020] of Patent Literature 1). Thus, this technique is capable of collecting only the sound coming from the front and the voice uttered by the user. Also, in the technique disclosed by Patent Literature 2, sound coming from the front is reverberated by an ear cover and is then collected to the user's ear (see paragraph [0009] of Patent Literature 2). Thus, this technique is capable of collecting only the sound coming from the front. Meanwhile, for example, increasing auditory sensitivity with respect to sound coming from the rear leads to enhancement of concentration and attentiveness in a rear direction. This also applies to sound coming from the left, sound coming from the right, sound coming from upward, sound coming from downward, and sound coming from other directions. However, both of the techniques disclosed by Patent Literatures 1 and 2 are directed to increasing a sound collection effect with respect to sound coming from a particular direction (for example, the front). Therefore, these techniques involve a problem of difficulty in enhancement of concentration and attentiveness in any direction.

Focusing on such an unsolved problem of the known techniques, the present invention has been made. Namely, the present invention has an object to provide an auditory sensitivity adjustment device suitable to enhance concentration and attentiveness in any direction.

Solutions to the Problems

Embodiment 1

In order to achieve the above described object, an auditory sensitivity adjustment device for adjusting auditory sensitivity of a human or an animal according to the embodiment 1, includes: a pinna holding unit for holding a pinna of a human or an animal; a pinna pulling unit for pulling, in an extending direction, the pinna held by the pinna holding unit; and a pinna moving unit for twisting or swinging the pinna held by the pinna holding unit.

According to such a structure, the pinna is held by the pinna holding unit. Further, the pinna thus held is pulled by the pinna pulling unit in the extending direction. Furthermore, the pinna thus held is twisted or swung by the pinna moving unit. Namely, by moving the pinna by the pinna moving unit, it is possible to enhance auditory sensitivity with respect to sound coming from any direction. For example, in order to enhance auditory sensitivity with respect to sound coming from the rear, the pinna may be moved so that a front surface of the pinna faces rearward.

Note here that the expression "adjusting auditory sensitivity" means adjusting a degree of sound perception of a human or an animal by moving the pinna according to the present invention, rather than adjusting an auditory function that is intrinsic to a human or an animal.

Effect of the Invention

As described above, according to the auditory sensitivity adjustment device of Embodiment 1, it is possible to move the pinna by the pinna moving unit. This makes it possible to enhance auditory sensitivity with respect to sound coming from any direction. Thus, it is possible to enhance concentration and attentiveness in any direction, in contrast with the known techniques.

DESCRIPTION OF THE EMBODIMENTS

Figure 1:
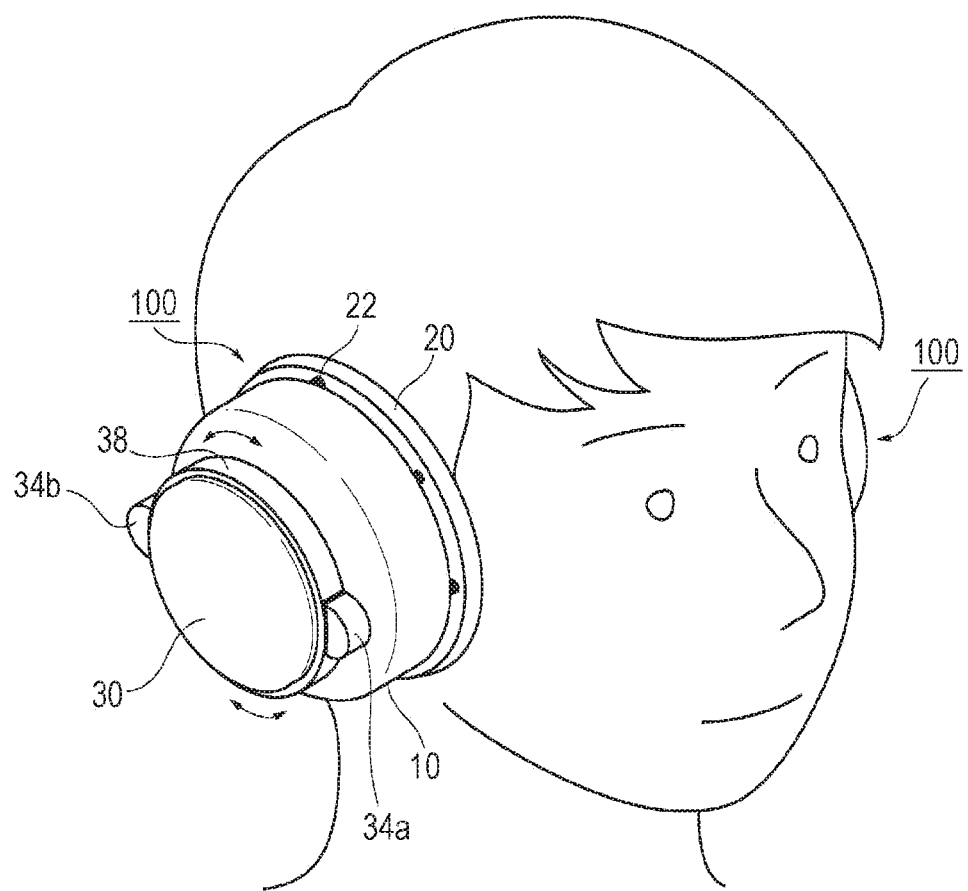
FIG. 1 is a perspective view illustrating a state where an auditory sensitivity adjustment device 100 is worn.
Figure 2:
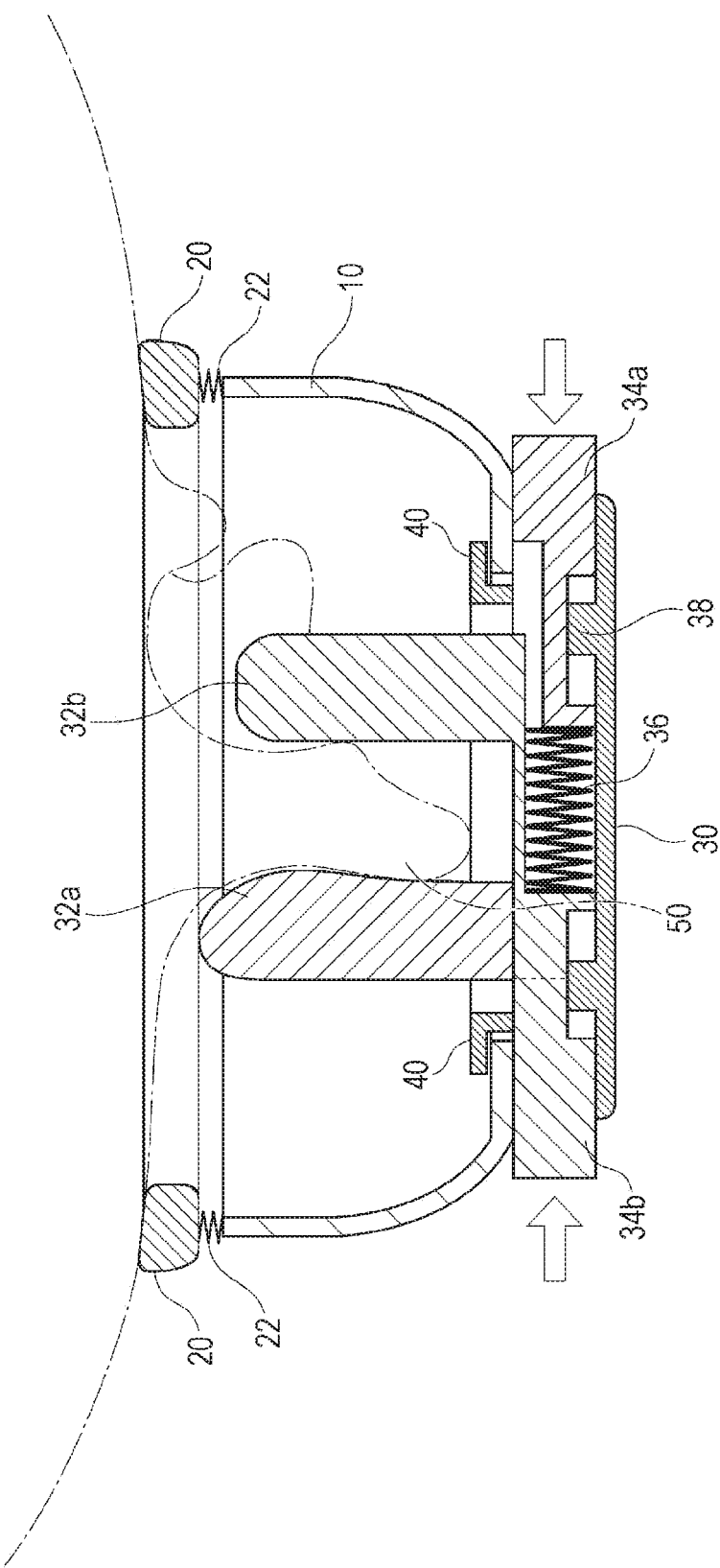
FIG. 2 is a cross-sectional view in a horizontal direction of the auditory sensitivity adjustment device 100 viewed from above.
Figure 3:
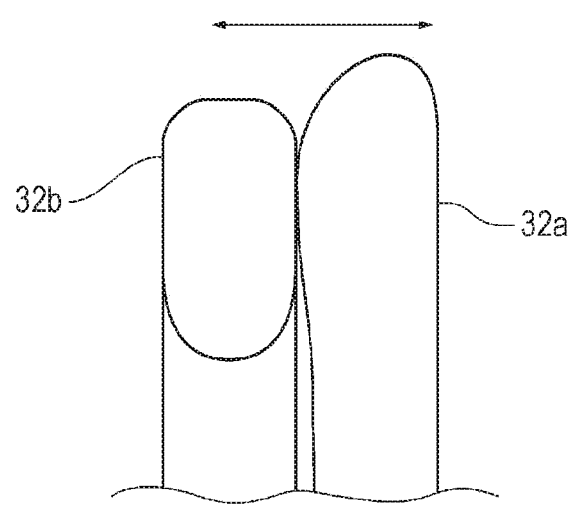
FIG. 3 is a plan view of grab parts 32a and 32b viewed from the bottom.

The following describes embodiments of the present invention. FIGS. 1 to 3 show the present embodiment.

First, the following describes a configuration of an auditory sensitivity adjustment device 100 according to the present embodiment.

FIG. 1 is a perspective view illustrating a state where the auditory sensitivity adjustment device 100 is worn. FIG. 2 is a cross-sectional view in a horizontal direction of the auditory sensitivity adjustment device 100 viewed from above. FIG. 3 is a plan view of grab parts 32a and 32b viewed from the bottom.

As shown in FIGS. 1 and 2, the auditory sensitivity adjustment device 100 includes a housing 10 shaped in a bowl, a cushion member 20 serving as a seat on which the housing 10 is placed, and a pinna holding part 30 for holding a pinna 50 of a human.

The housing 10 is made of a material through which external sound is easy to be transmitted. Alternatively, the housing 10 may have one or more small holes or windows through which external sound is transmitted.

The cushion member 20 is made of an elastic material such as a cushion. The cushion member 20 has an annular shape along the bottom of the housing 10. The cushion member 20 is attached to the bottom of the housing 10 via a plurality of springs 22. The springs 22 apply a biasing force for pulling in the extending direction the pinna 50 held by the pinna holding part 30.

The pinna holding part 30 includes a base 38 and a pair of grab parts 32a and 32b for holding the pinna 50.

The grab part 32a has an L-shape along the extending direction. Meanwhile, the grab part 32b has an inverted L-shape along the extending direction so as to be symmetric to the grab part 32a. The grab parts 32a and 32b are combined so as to intersect each other in such a manner that a terminal end 34a of the grab part 32a and a tip end (i.e., an end on a side for holding the pinna 50) of the grab part 32b are opposed to each other and that a terminal end 34b of the grab part 32b and a tip end (i.e., an end on a side for holding the pinna 50) of the grab part 32a are opposed to each other. There provided a spring 36 between an inner side of the terminal end 34a of the grab part 32a and an inner side of the terminal end 34b of the grab part 32b. The spring 36 applies a biasing force for causing the tip ends of the grab parts 32a and 32b to come close to each other and a biasing force for causing the terminal ends 34a and 34b of the grab parts 32a and 32b to separate from each other.

The grab parts 32a and 32b and the spring 36 are attached to the base 38. The terminal end 34a of the grab part 32a is protruded from one side opening of the base 38. The terminal end 34b of the grab part 32b is protruded from another side opening of the base 38, the side opening being opposite to the one side opening. Wearer's pushing the terminal ends 34a and 34b of the grab parts 32a and 32b, which are protruded from the base 38, allows the tip ends of the grab parts 32a and 32b to be opened. Wearer's releasing the pushing of the terminal ends 34a and 34b of the grab parts 32a and 32b allows the tip ends of the grab parts 32a and 32b to be closed due to a biasing force by the spring 36.

The housing 10 has an apex having an opening. Meanwhile, the base 38 has a bottom having a cylindrical shaft member 40 whose diameter is slightly smaller than that of the opening in the apex of the housing 10. The shaft member 40 has a tip end having a flange whose diameter is larger than that of the opening in the apex of the housing 10. The shaft member 40 is fitted into the opening in the apex of the housing 10. As a result of the fitting, the pinna holding part 30 is attached to the housing 10, the pinna holding part 30 is locked by the flange of the shaft member 40 such that the pinna holding part 30 would not be detached from the housing 10, and the pinna holding part 30 becomes rotatable around the shaft member 40 with respect to the housing 10.

As shown in FIG. 3, the tip end of the grab part 32a has a shape similar to a thumb of a human. The tip end of the grab part 32b has a shape similar to an index finger of a hand making a fist (i.e., an index finger curled with its first to third joints bent). The pinna 50 is held by the grab parts 32a and 32b with a biasing force of the spring 36 in such a manner that the pinna 50 is sandwiched by the tip end of the grab part 32a, positioned to face a back surface of the pinna 50, and the tip end of the grab part 32b, positioned to face a front surface of the pinna 50. Thus, the pinna 50 is held by the thumb and the index finger of the fist, and this makes the wearer feel as if the pinna 50 is held by a human's hand. This enables to reduce an uncomfortable feeling during wearing. For this reason, the tip ends of the grab parts 32a and 32b preferably have an elasticity equivalent to that of a human's finger.

Next, the following describes how the present embodiment operates.

First, a wearer pushes the terminal ends 34a and 34b of the grab parts 32a and 32b. In a state where the tip ends of the grab parts 32a and 32b are opened, the wearer holds the auditory sensitivity adjustment device 100. Subsequently, the wearer directs the cushion member 20 toward the pinna 50, and wears the auditory sensitivity adjustment device 100 in such a manner that the auditory sensitivity adjustment device 100 covers the pinna 50. At this time, the auditory sensitivity adjustment device 100 is worn so that the pinna 50 is located between the tip ends of the grab parts 32a and 32b. Then, the pushing of the terminal ends 34a and 34b of the grab parts 32a and 32b is released. Consequently, the tip ends of the grab parts 32a and 32b are closed by a biasing force of the spring 36. As a result, the pinna 50 is held by the grab parts 32a and 32b, and is pulled by a biasing force of the springs 22 in the extending direction.

For example, in order to enhance auditory sensitivity with respect to sound coming from upward, the pinna holding part 30 may be rotated counterclockwise. Rotating the pinna holding part 30 counterclockwise causes the pinna 50 held by the grab parts 32a and 32b to be twisted counterclockwise. As a result, the front surface of the pinna 50 slightly faces upward. This enhances auditory sensitivity with respect to sound coming from upward.

Meanwhile, for example, in order to enhance auditory sensitivity with respect to sound coming from downward, the pinna holding part 30 may be rotated clockwise. Rotating the pinna holding part 30 clockwise causes the pinna 50 held by the grab parts 32a and 32b to be twisted clockwise. As a result, the front surface of the pinna 50 slightly faces downward. This enhances auditory sensitivity with respect to sound coming from downward.

As described above, according to the present embodiment, the auditory sensitivity adjustment device 100 includes the grab parts 32a and 32b for holding the pinna 50, the springs 22, and the base 38. The springs 22 apply to the grab parts 32a and 32b a force for pulling, in the extending direction, the pinna 50 held by the grab parts 32a and 32b. The base 38 is rotated so that the pinna 50 held by the grab parts 32a and 32b is twisted.

Accordingly, it is possible to enhance auditory sensitivity with respect to sound coming from any direction. Thus, it is possible to enhance concentration and attentiveness in any direction, in contrast with the known techniques.

In the present embodiment, the springs 22 correspond to the pinna pulling unit of Embodiment 1, the grab parts 32a and 32b correspond to the pinna holding unit of Embodiment 1, and the base 38 corresponds to the pinna moving unit of Embodiment 1.

[Other Variations]

According to the above embodiment, the device is configured to twist the pinna 50. However, the device of the present invention is not limited to this, but can alternatively be configured to swing the pinna 50 around the base of the pinna 50, the base serving as a fulcrum. In such a configuration, the device may include a mechanism for causing the base 38 to slide in a back-and-forth direction (hereinafter, referred to as a "sliding mechanism"). Further alternatively, the device of the present invention can be configured to twist and swing the pinna 50. In such a configuration, the device may include the mechanism for making the base 38 rotatable with respect to the housing 10 and the sliding mechanism. Note here that the direction in which the sliding mechanism cause the base 38 to slide is not limited to a back-and-forth direction, but may alternatively be an up-and-down direction or any other direction. Further, the manner in which the sliding mechanism cause the base 38 to slide is not limited to a linear manner, but may alternatively be a curved manner.

According to the above embodiment and its variations, the device is configured such that the grab parts 32a and 32b are opened and closed manually. However, the device of the present invention is not limited to this, but can alternatively be configured such that the grab parts 32a and 32b are opened and closed automatically by a driving unit such as an actuator. Similarly, the base 38 can be rotated automatically, rather than manually. As for the sliding mechanism, the base 38 can be caused to slide automatically, rather than manually. In order to employ such an automated mechanism, the device can be configured, for example, such that a source of external sound collected by a microphone or the like is first identified, and then the rotation or the sliding of the base 38 is controlled to cause the front surface of the pinna 50 to face the identified source.

According to the above embodiment and its variations, the device is configured such that the pinna 50 is pulled by the grab parts 32a and 32b. However, the device of the present invention is not limited to this, but can alternatively be configured such that the pinna 50 is pulled by another member which is not the grab parts 32a and 32b. Namely, a member for directly pulling the pinna 50 can be the grab parts 32a and 32b or another member which is not the grab parts 32a and 32b.

According to the above embodiment and its variations, the device is configured such that the pinna 50 is twisted by the grab parts 32a and 32b. However, the device of the present invention is not limited to this, but can alternatively be configured such that the pinna 50 is twisted by another member which is not the grab parts 32a and 32b. Similarly, the device of the present invention can be arranged such that the pinna 50 is swung by another member which is not the grab parts 32a and 32b. Namely, a member for directly twisting or swinging the pinna 50 can be the grab parts 32a and 32b or another member which is not the grab parts 32a and 32b.

According to the above embodiment and its variations, the present invention is applied to cases where the pinna 50 of a human is held. However, the present invention is not limited to such cases, but can alternatively be applied to cases where a pinna of an animal is held.

LIST OF NUMERAL REFERENCES

100 Auditory sensitivity adjustment device
10 Housing
20 Cushion member
22 Spring
30 Pinna holding part
32a, 32b Grab parts
34a, 34b Terminal ends of grab parts
36 Spring
38 Base
40 Shaft member
50 Pinna

The invention claimed is:

1. An auditory sensitivity adjustment device for adjusting auditory sensitivity of a human or an animal, comprising:
    a pinna holding unit comprising a first spring applying a biasing force for holding a pinna of a human or an animal;
    a second spring applying a biasing force for pulling, in a direction away from the pinna, the pinna held by the pinna holding unit; and
    a pinna moving unit for twisting or swinging the pinna held by the pinna holding unit while the spring pulls the pinna,
    wherein a direction of the biasing force of the first spring is perpendicular to a direction of the biasing force of the second spring.

2. An auditory sensitivity adjustment device for adjusting auditory sensitivity of a human or an animal, comprising:
    a pinna holding unit for holding a pinna of a human or an animal;
    a spring for pulling, in a direction away from the pinna, the pinna held by the pinna holding unit;
    a pinna moving unit for twisting or swinging the pinna held by the pinna holding unit while the spring pulls the pinna;
    a housing comprising an apex having an opening; and
    a cylindrical shaft member having a first diameter smaller than a diameter of the opening, the shaft member comprising a flange having a second diameter larger than a diameter of the opening;
    wherein the pinna holding unit and the pinna moving unit are attached to the housing by fitting the shaft member into the opening.

3. The auditory sensitivity adjustment device according to claim 2, wherein the pinna holding member is capable of rotating around the shaft member with respect to the housing.

4. The auditory sensitivity adjustment device according to claim 2, wherein the pinna holding member is inserted into the shaft member and capable of rotating around an axis of the shaft member with respect to the housing.

* * * * *